(12) United States Patent
Tsadok et al.

(10) Patent No.: US 12,254,673 B1
(45) Date of Patent: Mar. 18, 2025

(54) SYSTEMS AND METHODS FOR CLASSIFYING OR SELECTING IMAGES BASED ON IMAGE SEGMENTATION

(71) Applicant: Given Imaging LTD, Yoqneam (IL)

(72) Inventors: Yossi Tsadok, Pardes Hanna-Karkur (IL); Dori Peleg, Kiryat Bialik (IL)

(73) Assignee: GIVEN IMAGING LTD, Yoqneam (IL)

( * ) Notice: Subject to any disclaimer, the term of this patent is extended or adjusted under 35 U.S.C. 154(b) by 435 days.

(21) Appl. No.: 17/543,985

(22) Filed: Dec. 7, 2021

Related U.S. Application Data

(60) Provisional application No. 63/138,905, filed on Jan. 19, 2021.

(51) Int. Cl.
| | | |
|---|---|---|
| *G06V 10/764* | (2022.01) | |
| *A61B 1/04* | (2006.01) | |
| *G06T 7/00* | (2017.01) | |
| *G06V 10/26* | (2022.01) | |
| *G06V 10/46* | (2022.01) | |

(Continued)

(52) U.S. Cl.
CPC ............ *G06V 10/765* (2022.01); *A61B 1/041* (2013.01); *G06T 7/0012* (2013.01); *G06V 10/267* (2022.01); *G06V 10/46* (2022.01); *G06V 10/762* (2022.01); *G06V 10/82* (2022.01); *G06T 2207/10068* (2013.01);
(Continued)

(58) Field of Classification Search
CPC .... G06V 10/765; G06V 10/267; G06V 10/46; G06V 10/762; G06V 10/82; G06V 2201/03; A61B 1/041; G06T 7/0012; G06T 2207/10068; G06T 2207/20084; G06T 2207/30028; G06T 2207/30092
See application file for complete search history.

(56) References Cited

U.S. PATENT DOCUMENTS

| | | | | |
|---|---|---|---|---|
| 8,682,142 B1 * | 3/2014 | Boskovitz | ............ | G11B 27/034 386/282 |
| 8,861,783 B1 * | 10/2014 | Peleg | ................ | A61B 1/000094 382/100 |

(Continued)

OTHER PUBLICATIONS

Johan Staaf et al. "Segmentation-based detection of allelic imbalance and loss-of-heterozygosity in cancer cells using whole genome SNP arrays", Genome Biology, vol. 9, Issue 9, pp. R136.1-R136.18 (2008).

(Continued)

*Primary Examiner* — Santiago Garcia
(74) *Attorney, Agent, or Firm* — Carter, DeLuca & Farrell LLP

(57) ABSTRACT

The present disclosure relates to classifying and/or selecting images based on image segmentation. A classification system for classifying images includes one or more processors and at least one memory storing machine executable instructions. When the instructions are executed by the one or more processors, they cause the classification system to: access image segmentation scores for pixels of an image, and classify the entire image based on the image segmentation scores for the pixels of the image. The image segmentation scores for the pixels of the image are provided by an image segmentation system based on the image, and each of the image segmentation scores correspond to at least one pixel of the pixels of the image.

18 Claims, 5 Drawing Sheets

610 — Access images of a gastrointestinal tract (GIT) captured by a capsule endoscopy device during a CE procedure.

620 — For each respective image of the images: access respective image segmentation scores for pixels of the respective image, where the respective image segmentation scores are provided by an image segmentation system based on the respective image, and each of the respective image segmentation scores corresponds to one or more pixels of the respective image.

630 — Select one or more images from among the images, for a capsule endoscopy study, based on the image segmentation scores corresponding to the images.

(51) Int. Cl.
*G06V 10/762* (2022.01)
*G06V 10/82* (2022.01)
(52) U.S. Cl.
CPC ............... *G06T 2207/20084* (2013.01); *G06T 2207/30028* (2013.01); *G06T 2207/30092* (2013.01); *G06V 2201/03* (2022.01)

(56) References Cited

U.S. PATENT DOCUMENTS

| | | | |
|---|---|---|---|
| 9,324,145 B1* | 4/2016 | Cherevatsky | A61B 1/000094 |
| 9,865,042 B2 | 1/2018 | Dai et al. | |
| 2012/0002879 A1* | 1/2012 | Kanda | G06T 7/11 |
| | | | 382/195 |
| 2014/0320620 A1* | 10/2014 | Ikemoto | G06T 7/90 |
| | | | 348/71 |
| 2015/0356730 A1* | 12/2015 | Grove | G06T 7/64 |
| | | | 382/124 |
| 2018/0182092 A1* | 6/2018 | Drozdzal | G06T 7/0012 |
| 2018/0306768 A1* | 10/2018 | Little | G01N 21/6456 |
| 2018/0330498 A1* | 11/2018 | Little | G01N 21/6456 |
| 2019/0056404 A1* | 2/2019 | Dakappagari | A61P 35/00 |
| 2019/0192048 A1* | 6/2019 | Makino | A61B 1/0638 |
| 2019/0365213 A1* | 12/2019 | Park | A61B 1/00193 |
| 2019/0370972 A1* | 12/2019 | Bagci | G06T 7/0012 |
| 2020/0053268 A1* | 2/2020 | Hirota | G06T 7/586 |
| 2020/0090008 A1* | 3/2020 | Choi | G06V 10/454 |
| 2021/0219829 A1* | 7/2021 | Liu | A61B 1/041 |
| 2021/0383262 A1* | 12/2021 | Elen | G06F 18/2163 |
| 2022/0028550 A1* | 1/2022 | Ng | A61B 1/000094 |
| 2022/0039357 A1* | 2/2022 | Roth | G06N 20/00 |
| 2022/0222914 A1* | 7/2022 | Pradhan | G06F 18/24133 |

OTHER PUBLICATIONS

Bharath Hariharan, et al., "Simultaneous Detection and Segmentation", ECCV 2014, Part VII, LNCS 8695, pp. 297-312 (2014).

Kenji Suzuki, et al., "Massive-Training Artificial Neural Networks for Cad for Detection of Polyps in CT Colonography: False-Negative Cases in a Large Multicenter Clinical Trial", ISBI, pp. 684-687 (2008).

S. Gould, et al., "Region-based Segmentation and Object Detection", pp. 1-9, Conference: Advances in Neural Information Processing Systems 22: 23rd Annual Conference on Neural Information Processing Systems, Dec. 7-10, 2009, Vancouver, Canada; retrieved Mar. 7, 2022 (https://ai.stanford.edu/~koller/Papers/Gould+aI:NIPS09.pdf).

Xi Mo, et al., "An Efficient Approach for Polyps Detection in Endoscopic Videos Based on Faster R-CNN", arXiv:1809.01263v1 [q-bio.TO] Sep. 4, 2018 (6 pages).

Jifeng Dai, et al, "R-FCN: Object Detection via Region-based Fully Convolutional Networks", arXiv:1605-06409v2 [cs.CV] Jun. 21, 2016 (11 pages).

Kaiming He, et al., "Mask R-CNN", arXiv:1703:06870v3 [cs.CV] Jan. 24, 2018 (12 pages).

Gökalp Tulum, et al., "A CAD of fully automated colonic polyp detection for contrasted and non-contrasted CT scans", Int J CARS (2017), 12:627-644 (18 pages).

Yu Tian, et al., "One-Stage Five-Class Polyp Detection and Classification", published in 2019 IEEE 16th International Symposium on Biomedical Imaging (ISBI 2019) (4 pages). (https://ieeexplore.ieee.org/abstract/document/8759521).

J. Bernal, et al. "Towards automatic polyp detection with a polyp appearance model", Pattern Recognition 45 (2012) 3166-3182 (17 pages).

Pradipta Sasmal, et al. "Classification of Polyps in Capsule Endoscopic Images using CNN", Proceedings of 2018 IEEE Applied Signal Processing Conference (ASPCON), 2018, pp. 253-256 (4 pages).

M. Arlt, et al., "Automated Polyp Differentiation on Coloscopic Data Using Semantic Segmentation With CNNS", Endoscopy 2019; 51(04): S4 (2 pages). (https://www.thieme-connect.com/products/ejournals/html/10.1055/s-0039-1681180).

* cited by examiner

210
For an image, access or generate image segmentation scores for pixels of the image.

220
Classifying the entire image based on the image segmentation scores for the pixels of the image.

| 0.08 | 0.01 | 0.02 | 0.01 | 0.05 | 0.01 | 0.01 | 0.08 | 0.1  | 0.06 |
|------|------|------|------|------|------|------|------|------|------|
| 0.05 | 0.05 | 0.07 | 0.01 | 0.1  | 0.08 | 0.04 | 0.06 | 0.03 | 0.03 |
| 0.22 | 0.29 | 0.24 | 0.26 | 0.23 | 0.04 | 0.01 | 0.09 | 0    | 0.1  |
| 0.5  | 0.5  | 0.43 | 0.48 | 0.29 | 0.02 | 0.03 | 0.01 | 0.07 | 0.03 |
| 0.48 | 0.91 | 0.91 | 0.42 | 0.25 | 0.01 | 0.08 | 0.05 | 0.07 | 0.05 |
| 0.42 | 1    | 0.94 | 0.45 | 0.25 | 0.06 | 0.02 | 0.03 | 0.02 | 0.06 |
| 0.46 | 0.5  | 0.43 | 0.48 | 0.22 | 0.07 | 0.07 | 0.09 | 0.01 | 0.05 |
| 0.21 | 0.23 | 0.21 | 0.26 | 0.23 | 0.04 | 0.07 | 0.04 | 0.04 | 0.1  |
| 0.07 | 0.02 | 0.05 | 0.07 | 0.09 | 0.09 | 0.07 | 0.06 | 0.09 | 0.06 |
| 0.09 | 0.04 | 0.07 | 0.05 | 0.06 | 0.02 | 0.05 | 0.02 | 0.02 | 0.02 |

FIG. 3

422 ─┐
Transform the image segmentation scores for pixels of the image to provide one or more image classification scores for the image.

424 ─┐
Classify the entire image based on at least one of the image classification scores for the image.

FIG. 4

522 ─┐
Access image segmentation scores for pixels of an image.

524 ─┐
Determine a shape of pixels indicated to be pixels of interest based on the image segmentation scores, and/or determine a distribution of pixels indicated to be the pixels of interest based on the image segmentation scores.

536 ─┐
Classify the entire image based on at least one of the determined shape or the determined distribution.

FIG. 5

SYSTEMS AND METHODS FOR CLASSIFYING OR SELECTING IMAGES BASED ON IMAGE SEGMENTATION

CROSS-REFERENCE TO RELATED APPLICATIONS

This application claims the benefit of and priority to U.S. Provisional Patent Application No. 63/138,905, filed Jan. 19, 2021, which is hereby incorporated by reference herein in its entirety.

FIELD

The disclosure relates to image classification and, more particularly, to systems and methods for classifying and/or selecting images based on image segmentation.

BACKGROUND

Image Classification may be defined as a fundamental task that attempts to comprehend an entire image as a whole. The aim is to classify the image by assigning it to a specific label. Accordingly, an image may be classified, for example, as containing a cat, a dog or both, or neither. With respect to medical images, image classification may be used to determine whether or not an image contains an anatomical feature or an indicator of a disease, pathology, or condition, among other things. For example, image classification may be used to determine whether an x-ray image shows a bone fracture, whether a computed tomography (CT) image shows a tumor, or whether a magnetic resonance image (MRI) shows indications of a stroke, among other applications.

Machine learning technology has been widely adopted in the field of image classification. For example, convolutional neural networks have been widely tested for image classification tasks. Machine-learning based systems have made great strides in improving the accuracy of image detection systems. For real-world deployment of image classification systems, greater accuracy is always desirable. There is room for further improvement and, accordingly, there is continued interest in developing improved image classification systems.

SUMMARY

The present disclosure relates to systems and methods for classifying and/or selecting images based on image segmentation. In various aspects, the present disclosure relates to transforming image segmentation scores provided by an image segmentation system into one or more image classification scores, and classifying the entire image based on the image classification score(s). In various aspects, the systems and methods of the present disclosure can be applied to classify and/or select medical images and images captured by a capsule endoscopy device of a capsule endoscopy procedure, in particular.

In an aspect of the present disclosure, a classification system for classifying images includes one or more processors and at least one memory storing machine executable instructions. The instructions, when executed by the one or more processors, cause the classification system to: access image segmentation scores for pixels of an image, and classify the entire image based on the image segmentation scores for the pixels of the image. The image segmentation scores are provided by an image segmentation system based on the image, and each of the image segmentation scores correspond to at least one pixel of the pixels of the image.

In various embodiments of the classification system, the instructions, when executed by the one or more processors, further cause the classification system to transform the image segmentation scores for the pixels of the image to provide at least one image classification score, where classifying the entire image includes classifying the image based on at least the at least one image classification score.

In various embodiments of the classification system, in transforming the image segmentation scores, the instructions, when executed by the one or more processors, cause the classification system to perform at least one of: an inference of a machine learning classifier or a non-machine learning transformation operation.

In various embodiments of the classification system, the non-machine learning transformation operation includes determining a maximum score among the image segmentation scores for the pixels of the image, where classifying the entire image includes classifying the entire image based on the maximum score.

In various embodiments of the classification system, the non-machine learning transformation operation includes determining at least one of: an average score of a predetermined number of highest image segmentation scores among the image segmentation scores for the pixels of the image, or a count of the image segmentation scores for the pixels of the image having a value above a threshold, where classifying the entire image includes classifying the entire image based on at least one of: the average score or the count.

In various embodiments of the classification system, the non-machine learning transformation operation includes: identifying a cluster of pixels of the image corresponding to a cluster of highest image segmentation scores among the image segmentation scores for the pixels of the image, and determining an average score of the cluster of highest image segmentation scores, where classifying the entire image includes classifying the entire image based on the average score of the cluster.

In various embodiments of the classification system, the image segmentation scores for the pixels of the image include scores indicating whether a pixel is a background pixel or a pixel of interest. The instructions, when executed by the one or more processors, cause the classification system to further perform at least one of: determining a shape of pixels indicated to be pixels of interest based on the image segmentation scores, or determining a distribution of pixels indicated to be pixels of interest based on the image segmentation scores, where classifying the entire image includes classifying the entire image based on at least one of: the determined shape or the determined distribution.

In various embodiments of the classification system, the instructions, when executed by the one or more processors, further cause the classification system to input the image to a deep learning neural network to generate the image segmentation scores.

In various embodiments of the classification system, each score of the image segmentation scores corresponds to one pixel of the pixels of the image.

In accordance with aspects of the present disclosure, a classification method for classifying images includes: accessing image segmentation scores for pixels of an image, and classifying the entire image based on the image segmentation scores for the pixels of the image. The image segmentation scores are provided by an image segmentation system based on the image, and each of the image segmentation scores corresponds to at least one pixel of the pixels of the image.

In various embodiments of the classification method, the classification method includes transforming the image segmentation scores for the pixels of the image to provide at least one image classification score, where classifying the entire image includes classifying the entire image based on at least the at least one image classification score.

In various embodiments of the classification method, transforming the image segmentation scores includes performing at least one of: an inference of a machine learning classifier or a non-machine learning transformation operation.

In various embodiments of the classification method, the non-machine learning transformation operation includes determining a maximum score among the image segmentation scores for the pixels of the image, where classifying the entire image includes classifying the entire image based on the maximum score.

In various embodiments of the classification method, the non-machine learning transformation operation includes determining at least one of: an average score of a predetermined number of highest image segmentation scores among the image segmentation scores for the pixels of the image, or a count of the image segmentation scores for the pixels of the image having a value above a threshold, where classifying the entire image includes classifying the entire image based on at least one of: the average score or the count.

In various embodiments of the classification method, the non-machine learning transformation operation includes: identifying a cluster of pixels of the image corresponding to a cluster of highest image segmentation scores among the image segmentation scores for the pixels of the image, and determining an average score of the cluster of highest image segmentation scores, where classifying the entire image comprises classifying the entire image based on the average score of the cluster.

In various embodiments of the classification method, the image segmentation scores for the pixels of the image include scores indicating whether a pixel is a background pixel or a pixel of interest. The method includes performing at least one of: determining a shape of pixels indicated to be pixels of interest based on the image segmentation scores, or determining a distribution of pixels indicated to be pixels of interest based on the image segmentation scores, where classifying the entire image comprises classifying the entire image based on at least one of: the determined shape or the determined distribution.

In various embodiments of the classification method, the classification method includes inputting the image to a deep learning neural network to generate the image segmentation scores.

In various embodiments of the classification method, each score of the image segmentation scores corresponds to one pixel of the pixels of the image.

In accordance with aspects of the present disclosure, an image selection system for selecting images of a gastrointestinal tract includes one or more processors and at least one memory storing machine executable instructions. The instructions, when executed by the one or more processors, cause the image selection system to: access a plurality of images of a gastrointestinal tract (GIT) captured by a capsule endoscopy device during a capsule endoscopy procedure; for each respective image of the plurality of images: access respective image segmentation scores for pixels of the respective image, where the respective image segmentation scores are provided by an image segmentation system based on the respective image, and each of the respective image segmentation scores correspond to at least one pixel of the pixels of the respective image; and select at least one image from among the plurality of images for a capsule endoscopy report based on the image segmentation scores corresponding to the plurality of images.

In various embodiments of the image selection system, the instructions, when executed by the one or more processors, further cause the image selection system to: for each image of the plurality of images: compute at least one respective image classification score for the respective image based on at least the respective image segmentation scores for the pixels of the respective image, where selecting at least one image from among the plurality of images based on the respective image segmentation scores includes selecting at least one image from among the plurality of images for the capsule endoscopy report based on at least at least the image classification scores computed from the image segmentation scores corresponding to the plurality of images.

In various embodiments of the image selection system, the instructions, when executed by the one or more processors, further cause the image selection system to: for each respective image of the plurality of images, compute respective information based on the respective image segmentation scores for the pixels of the respective image. In selecting at least one image from among the plurality of images for a capsule endoscopy study, the instructions, when executed by the one or more processors, cause the image selection system to select the at least one image based on the computed information for the plurality of images.

In various embodiments of the image selection system, an element of interest in the plurality of images is at most 30% of the pixels of a respective image.

Further details and aspects of exemplary embodiments of the present disclosure are described in more detail below with reference to the appended figures.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

FIG. 2 is a flow diagram of an exemplary operation for classifying an image based on image segmentation scores, in accordance with aspects of the present disclosure;

FIG. 3 is a diagram of an exemplary map of image segmentation scores, in accordance with aspects of the present disclosure;

FIG. 4 is a flow diagram of another exemplary operation for classifying an image based on image segmentation scores, in accordance with aspects of the present disclosure;

FIG. 5 is a flow diagram of yet another exemplary operation for classifying an image based on image segmentation scores, in accordance with aspects of the present disclosure;

DETAILED DESCRIPTION

Figure 1:
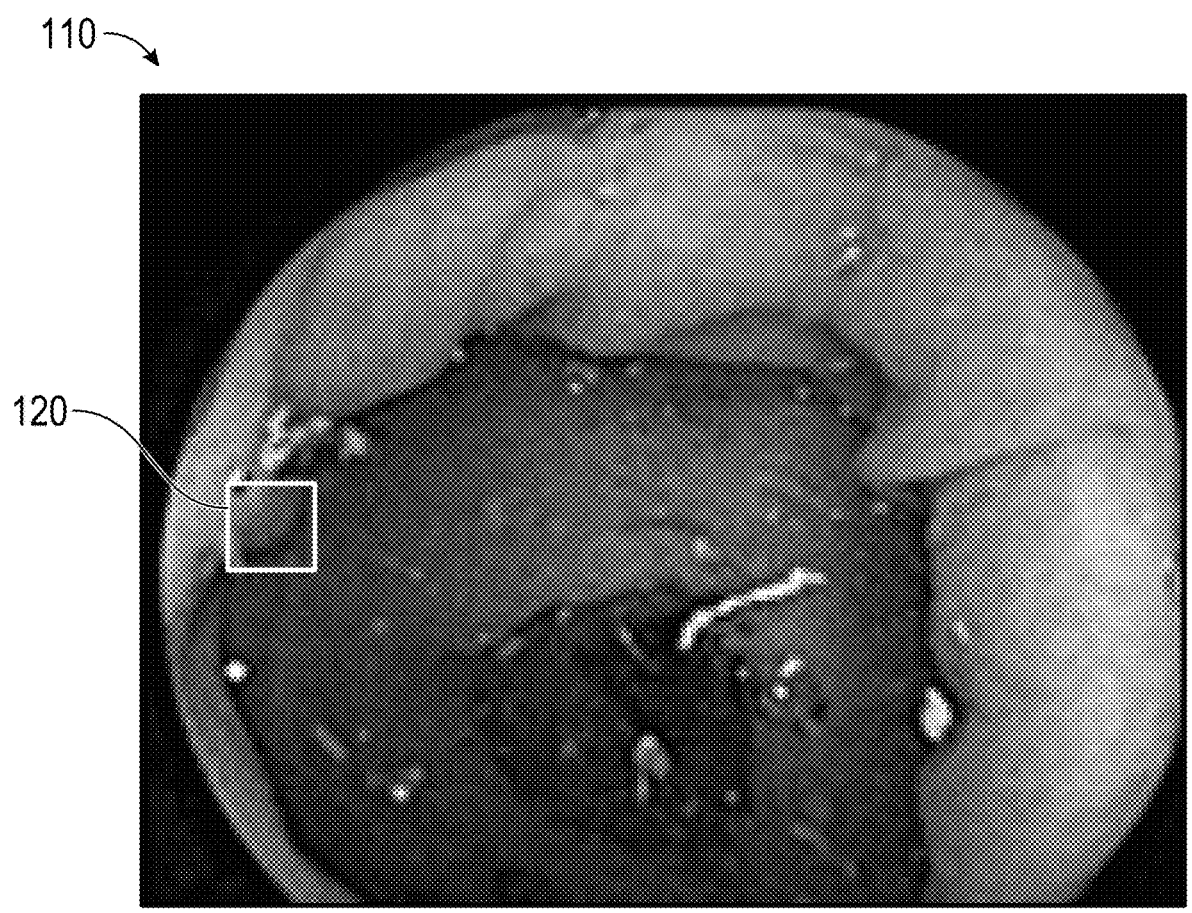
FIG. 1 is an exemplary image having an object of interest, in accordance with aspects of the present disclosure.

The disclosure relates to systems and methods for classifying and/or selecting images based on image segmentation. In various aspects, the present disclosure relates to transforming image segmentation scores provided by an image segmentation system into one or more values, properties, and/or image classification scores, and classifying an entire image or selecting an image based on the values, properties, and/or image classification score(s), among other possible tasks. In the description below, the phrase "classify an image," and its variants, may be used as a shorthand for classifying the entire image. Accordingly, any reference to classifying an image shall be understood to mean classifying an entire image. In various aspects, the systems and methods of the present disclosure can be applied to classify and/or select medical images or images captured by a capsule endoscopy device of a capsule endoscopy procedure. The values and/or properties described below herein (e.g., maximum, count of image segmentation scores above threshold, average of a cluster, weighted average of a cluster, shape of a cluster, shape encompassing image segmentation scores above a threshold, distribution of image segmentation scores above a threshold, among others), which are determined based on image segmentation scores, may be used for at least one of: determining a classification score, classifying an image, and/or selecting images for a CE study. For the tasks of classifying an image, selecting images for a CE study, selecting images for another purpose, or for another type of task, each such task may be performed based on classification scores and/or based on the values and/or properties disclosed herein. In various embodiments, as described below herein, the classification scores may be determined based on the image segmentation scores and optionally may be based on one or more of the values and/or properties. An image then may be classified based on the classification score. In various embodiments, the image may be classified also based on one or more the values and/or properties, which are determined based on image segmentation scores. In various embodiments, an image may be classified based on classification scores together with certain values and/or properties. In various embodiments, the values and/or properties, which are determined based on image segmentation scores, may be used for other purposes, such as image selection for CE study, localization of objects of interest, and/or tracking objects of interest, among other things.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of the same or similar features or elements may not be repeated.

Although the disclosure is not limited in this regard, discussions utilizing terms such as, for example, "processing," "computing," "determining," "calculating," "transforming," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Although the disclosure is not limited in this regard, the terms "plurality" and "a plurality" as used herein may include, for example, "multiple" or "two or more." The terms "plurality" or "a plurality" may be used throughout the specification to describe two or more components, devices, elements, units, parameters, or the like. The term "set," when used herein, may include one or more items. Unless explicitly stated, the methods described herein are not constrained to a particular order or sequence. Additionally, some of the described methods or elements thereof can occur or be performed simultaneously, at the same point in time, or concurrently.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classification score(s)" or "score(s)" may be used throughout the specification to indicate a value or a vector of values for a category or a set of categories applicable to an image/frame. In various implementations, the value or vector of values of a classification score or classification scores may be or may reflect probabilities. The model providing a classification score may be a machine learning system or may be a non-machine learning system. In various embodiments, a model may output classification scores which may be probabilities. In various embodiments, a model may output classification scores which may not be probabilities.

As used herein, a "machine learning system" means and includes any computing system that implements any type of machine learning. As used herein, "deep learning neural network" refers to and includes a neural network having several hidden layers and which does not require feature selection or feature engineering. A "classical" machine learning system, in contrast, is a machine learning system which requires feature selection or feature engineering. As used herein, an "inference" of a machine learning system refers to and includes operating a trained machine learning system to provide an output. In relation to a machine learning classifier that classifies an entire image, an inference refers to and includes operating the training machine learning classifier to infer the classification of an entire image.

The following detailed description may refer to a gastrointestinal tract as "GIT." As used herein, the term "GIT" may refer to the entire gastrointestinal tract or a portion of the gastrointestinal tract, according to the context. Disclosure relating to an entire GIT is intended to be applicable to a portion of the GIT, and vice versa.

Examples disclosed in the present disclosure may refer to capsule endoscopy, which is a procedure for examining a GIT endoscopically. It will be understood that references to capsule endoscopy are merely exemplary. The present disclosure may be applied to other imaging technologies and to other types of images. For example, the systems and methods of the present disclosure may apply to medical images or to non-medical images and may apply to the medical field or to any non-medical field. As examples of non-medical images of non-medical fields, the systems and methods of the present disclosure may analyze, classify and/or select surveillance images for security purposes, may analyze, classify and/or select galactic images for astronomy purposes, and may analyze, classify and/or select manufacturing images for quality assurance purposes, among other things. As examples of medical images, the systems and methods of the present disclosure may determine whether an x-ray image shows a bone fracture, whether a computed tomography (CT) image shows a tumor, or whether a magnetic resonance image (MRI) shows indications of a stroke, among other applications. Such and other applications are contemplated to be within the scope of the present disclosure.

Referring now to capsule endoscopy, capsule endoscopy is a non-invasive procedure in which a patient swallows a capsule including an imaging device. The capsule captures images as it travels naturally through the patient's GIT.

Typically, the number of images captured by the capsule and transferred to be processed is on the order of tens of thousands and about 90,000 images on average. The received images are then processed by an engine to a compiled study (or "study"). Typically, a study includes thousands of images, such as around 6,000 images, which were selected by the engine to be included in the study.

A reader (which may be the procedure supervising physician, a dedicated physician, or the referring physician) may then review the study, evaluate the procedure, and provide his input via a reader application. A report is then generated by the reader application based on the compiled study and the reader's input. On average, it would take an hour to review the study and generate a report. Thus, one of the goals of new developments in CE technology is to generate a study including as less images as possible. Examples for such new developments in generating and displaying a study are described in co-pending International Patent Application Publication No. WO/2020/079696, entitled "Systems and Methods for Generating and Displaying a Study of a Stream of In-Vivo Images," which is hereby incorporated by reference in its entirety. Reviewing thousands of images is a tedious task and may cause the reader to miss important information. Nevertheless, it is crucial that all images of medical importance will be included in the study. Accordingly, the processing and selection of CE images to be included in a CE study is very challenging and must be highly accurate, providing high sensitivity and specificity.

As described above, it will be understood that references to capsule endoscopy are merely exemplary. As mentioned above, the present disclosure may be applied to other types of images captured by other imaging technologies, including other types of medical images and non-medical images.

Referring now to FIG. 1, there is shown an exemplary image of a portion of a GIT captured by a capsule endoscopy (CE) device in a CE procedure. In certain situations, objects of interest a CE image, such as GIT pathologies and disease indicators, may be of relatively small size with respect to the image size. Furthermore, the color attributes of such GIT pathologies and disease indicators in such situations may not differ significantly from the color attributes of the surrounding tissue. All of the above may make the task of identifying CE images of interest quite difficult. The image 110 may show an anatomical feature or an indicator of a disease, pathology, or condition, among other things. In the illustrated image 110, a portion of the image includes a tissue growth of interest 120 which may indicate a possible disease, pathology, or condition. The tissue growth 120 occupies a relatively small portion of the image 110, such as about 1-5% of the image 110. Additionally, the color attributes of the tissue growth 120 may not differ significantly from the color attributes of the surrounding tissue. In these types of situations, typical image classification techniques may have difficulty in consistently and accurately classifying such an image 110 as containing an indicator of possible disease, pathology, or condition. As explained in more detail below, the disclosed systems and methods for classifying an image based on image segmentation for the image may be especially advantageous when the object of interest in an image occupies less than about 25%-30% of the image pixels. In various embodiments, the disclosed systems and methods may be particularly suitable when the object of interest in an image occupies less than about 10%-15% of the image pixels. Furthermore, the disclosed systems and methods for classifying an image based on image segmentation for the image may be also advantageous where the objects of interest in the image are characterized by color attributes or other image features which typically may not differ significantly from the color attributes or other image features of their surrounding or of the image background.

FIG. 2 shows a block diagram of an exemplary operation of classifying an image, in accordance with aspects of the present disclosure. At block 210, the operation involves, for an image, accessing or generating image segmentation scores for pixels of the image. In various embodiments, each pixel of the image may be assigned with a segmentation score. In various embodiments, each pixel has a distinct image segmentation score such that each image segmentation score corresponds to a single pixel. The image segmentation scores are generated by an image segmentation system. As persons skilled in the art will understand, an image segmentation system is a system which operates to indicate which pixels of an image may be pixels of interest and which pixels of an image may not be pixels of interest. With respect to the exemplary image 110 of FIG. 1, the pixels of the tissue growth 120 would be pixels of interest, and the other pixels of the image 110 would not be pixels of interest. The term "background pixel" may be used herein to indicate a pixel which is not a pixel of interest. Assuming the image 110 of FIG. 1 contains only one tissue growth 120, all of the pixels except the pixels of the tissue growth 120 would be background pixels. Examples of image segmentation systems include fully convolutional deep-learning neural networks, the U-Net network developed by Olaf Ronneberger et al., and the RefineNet network developed by Guosheng Lin et al., among others. FIG. 3 will be described later herein regarding the output of an image segmentation system. For now, it is sufficient to note that block 210 accesses or generates image segmentation scores for the pixels of an image, and each image segmentation score may correspond to one pixel or correspond to multiple pixels.

At block 220, the operation involves classifying the entire image based on the image segmentation scores for the pixels of the image. Various embodiments of block 220 for classifying the entire image based on the image segmentation scores for the pixels of the image will be described later herein. Generally, the operation of block 220 can classify the image as an image which contains a particular anatomical feature, or as an image which contains a particular indicator of a disease, pathology, or condition, among other things, or as an image which does not contain any anatomical feature of interest, or as an image which does not contain any indicators of interest, among other possibilities. All such possibilities are contemplated to be within the scope of the present disclosure.

FIG. 3 shows an exemplary map of image segmentation scores 310 for pixels of an image. The image segmentation scores 310 can correspond to pixels of the image 110 of FIG. 1, for example. The 10×10 grid of image segmentation scores is merely exemplary, and other grid/map sizes are within the scope of the present disclosure. Each image segmentation score can correspond to one or more pixels of the image. In the case where each pixel of the image has a distinct image segmentation score, such a map provides the highest resolution of image segmentation scores for the image. In other cases, each image segmentation score can correspond to multiple pixels, such as four pixels or another number of pixels per image segmentation score, and such a map provides a reduced resolution of image segmentation scores for the image. In the latter case, an image segmentation map with reduced resolution may be sufficient for various applications, while reducing computational and memory requirements.

In the illustrated embodiment, each image segmentation score can indicate a probability that the corresponding pixel(s) are pixels of interest. Thus, for example, a higher image segmentation score closer to one indicates that the corresponding pixel(s) are more likely to be pixels of interest, whereas a lower image segmentation score closer to zero indicates that the corresponding pixel(s) are more likely to not be pixels of interest (i.e., more likely to be background pixels). In the example of FIG. 3, the image segmentation scores 320 are highest and closest to one, which indicates that their corresponding pixels are pixels of interest. Because image segmentation scores provide information for each pixel of an image, using image segmentation scores for classifying an entire image may benefit from such per-pixel information and result in more accurate classification. Additionally, as explained in more detail below, the image segmentation scores may also be used to provide additional information that may be useful for other tasks, such as object size estimation or object tracking across images. Further, in cases where an operation involves both image segmentation and classification tasks, using image segmentation for the classification tasks may provide a reduction in computing resources compared to implementations which use separate machine learning models to perform the classification tasks.

The illustrated embodiment of FIG. 3 is exemplary, and variations are contemplated to be within the scope of the present disclosure. For example, in various embodiments, the meaning of the score values may be flipped, such that a higher image segmentation score indicates that the corresponding pixel(s) are more likely to be background pixels, whereas a lower image segmentation score indicates that the corresponding pixel(s) are more likely to be pixels of interest. In various embodiments, the image segmentation scores may not be normalized and may have values below zero and/or above one. In various embodiments, each location of the map 310 may have a vector of image segmentation scores (not shown). For example, at each map location, the vector of image segmentation scores may include SoftMax values such that the image segmentation scores of the vector sum to one. As persons skilled in the art will recognize, SoftMax is a function that converts a vector z of K real values (which may be negative, zero, positive, or greater than one) into a vector z' of K real values that sum to 1. Additionally, the SoftMax function can be applied in various ways, as persons skilled in the art will understand. Other variations are contemplated to be within the scope of the present disclosure.

As mentioned above, there are various embodiments of block 220 (FIG. 2) for classifying the entire image based on the image segmentation scores for the pixels of the image. FIG. 4 is a flow diagram of such an exemplary operation.

At block 422, the operation involves transforming the image segmentation scores for pixels of the image to provide one or more image classification scores for the image. In various embodiments, the transformation of the image segmentation scores for the pixels of the image into one or more classification scores for the image may use a machine learning system. For example, the image segmentation scores may be input to a machine learning system, which may perform computations to generate the one or more image classification scores. In various embodiments, transformation of the image segmentation scores for the pixels of the image into one or more classification scores for the image may use non-machine learning transformation operations. In various embodiments, the transformation of the image segmentation scores for the pixels of the image into one or more classification scores for classifying the entire image may include multiple operations, and certain operations may use a machine learning system while certain operations may be non-machine learning operations. The described embodiments are exemplary, and variations are contemplated to be within the scope of the present disclosure. For example, in various embodiments, a transformation may use more than one machine learning system and/or more than one non-machine learning transformation operations. Such and other variations are contemplated to be within the scope of the present disclosure.

With continuing reference to block 422, the image classification score(s) provided by the transformation may be various types of image classification scores. In various embodiments, the image classification scores can include a classification score indicative of presence of an element (e.g., an animal, a person, an object, the sky) or image characteristic of interest (e.g., a specific color). For example, in a medical image, the image classification scores can include a classification score indicative of presence of one or more anatomical feature or indicative of presence of one or more indicators of a disease, pathology, or condition, among other things. In various embodiments, the image classification scores can include a classification score indicative of absence of an element or image characteristic of interest. For example, in a medical image, the image classification scores can include a classification score indicative of absence of one or more anatomical features or indicative of absence of one or more indicators of a disease, pathology, or condition, among other things. With reference to medical images, in various embodiments, the image classification scores can include different classifications scores indicative of presence or absence of different anatomical features. In various embodiments, the image classification scores can include different classifications scores indicative of presence or absence of different indicators of the same diseases, pathologies, or conditions, or indicative of presence or absence of different indicators of different diseases, pathologies, or conditions. The described possibilities are exemplary, and variations are contemplated to be within the scope of the present disclosure.

At block 424, the operation involves classifying the entire image based on at least one of the image classification scores for the image. With continuing reference to the examples mentioned above, the operation of block 424 can classify the image as an image which contains presence of an element (e.g., an animal, a person, an object, the sky), or image characteristic of interest (e.g., a specific color), or a particular anatomical feature, or as an image which contains a particular indicator of a disease, pathology, or condition, among other things, or as an image which does not contain any anatomical feature of interest, or as an image which does not contain any indicators of interest (e.g., any element or characteristic of interest), among other possibilities. All such possibilities are contemplated to be within the scope of the present disclosure.

Referring again to block 422, various embodiments will now be described for non-machine learning transformation operations which transform the image segmentation scores for the pixels of the image into one or more values, properties, or classification scores for classifying the image and/or for selecting the image, among other possible tasks. The values and/or properties described below (e.g., maximum, count of scores above threshold, average of a cluster, weighted average of a cluster, shape of a cluster), which are determined based on image segmentation scores, may be used for at least one of: determining the classification score, classifying the image, and/or selecting images for a CE study. The embodiments described below can be implemented separately, or two or more of the embodiments can be implemented in combination. Additionally, while the examples below refer to the illustrated embodiment of FIG. 3, in which each pixel has a single score, the examples below may also be applied to implementations where each pixel is associated with a vector of image segmentation scores rather than a single score. In the case of a vector of image segmentation scores, each image segmentation score of the vector may correspond to a different category. For example, suppose an image may contain cats, dogs, or sky. Each pixel may be associated with a vector $[S_c, S_d, S_s]$, where $S_c$ is an image segmentation score indicating whether a pixel corresponds to a pixel of a cat, $S_d$ is an image segmentation score indicating whether a pixel corresponds to a pixel of a dog, and $S_s$ is an image segmentation score indicating whether a pixel corresponds to a pixel of a sky. Such example is merely illustrative, and other embodiments involving different categories and/or involving medical images or non-medical images are contemplated to be within the scope of the present disclosure.

In accordance with aspects of the present disclosure, the non-machine learning transformation operation can be an operation which determines a maximum score among the image segmentation scores for the pixels of the image. In the example of FIG. 3, the maximum score is "1." The maximum score can be an image classification score provided by the transformation operation and can be used to classify the entire image. In various embodiments, an image classification score may not be the same as the maximum score but may be based on the maximum score.

In accordance with aspects of the present disclosure, the non-machine learning transformation operation can be an operation which determines an average score of a predetermined number of highest image segmentation scores among the image segmentation scores for the pixels of the image. In the example of FIG. 3, for a predetermined number of six highest image segmentation scores, the average score is $(0.5+0.5+0.91+0.91+0.94+1)/6 \approx 0.793$. The number six is exemplary, and in various embodiments, the predetermined number of highest image segmentation scores can be another number. The average score can be an image classification score provided by the transformation operation and can be used to classify the entire image. In various embodiments, an image classification score may not be the same as the average score but may be based on the average score. In various embodiments, the average score may not be used to determine an image classification score but still may be used for classifying the image (e.g., in addition to the image classification score) or for other purposes, such as for selecting images, e.g., to be included in a CE study.

In accordance with aspects of the present disclosure, the non-machine learning transformation operation can be an operation which determines a count of the image segmentation scores for the pixels of the image having a value above a threshold. In the example of FIG. 3, for a threshold value of 0.9, the count of the image segmentation scores above 0.9 is four (4). The threshold value of 0.9 is exemplary and, in various embodiments, the threshold value can be another number. The count can be an image classification score provided by the transformation operation and can be used to classify the entire image. In various embodiments, an image classification score may not be the same as the count but may be based on the count. In various embodiments, the count may not be used to determine an image classification score but may be used, e.g., in addition to the image classification score, for classifying the image. In various embodiments, the count may be used for other purposes, such as for selecting images, e.g., to be included in a CE study. In various embodiments, the count of the image segmentation scores having a value above a threshold can be used to estimate a size of an object of interest in an image. In the case where the object of interest is a polyp, for example, the estimated size of the polyp may be useful information for a healthcare professional to consider. In various embodiments, the size of an object of interest in an image may be determined in another manner. In various embodiments, the size of an object of interest determined based on the count of segmentation scores above a threshold may be used to determine a classification score for the image, to classify the image and/or to select images for a CE study.

In accordance with aspects of the present disclosure, the non-machine learning transformation operation can be an operation which identifies a cluster of pixels of the image corresponding to a cluster of highest image segmentation scores among the image segmentation scores for the pixels of the image, and determines an average score or weighted average of the cluster of highest image segmentation scores. In the example of FIG. 3, the image segmentation scores 320 are a cluster of highest image segmentation scores and their average value is $(0.91+0.91+0.94+1)/4=0.94$. A weighted average may also be used. The average score or weighted average of the cluster can be an image classification score provided by the transformation operation and can be used to classify the entire image. In various embodiments, an image classification score may not be the same as the average score or the weighted average of the cluster but may be based on the average score or weighted average of the cluster. In various embodiments, the average score or weighted average score may not be used to determine an image classification score but may be used for classifying the image, e.g., in addition to the image classification score. In various embodiments, the average score or weighted average score may be used for other purposes, such as for image selection, e.g., to be included in a CE study. In various embodiments, a cluster can be identified in different ways. For example, in various embodiments, a cluster may be contiguous, and in various embodiments, a cluster need not be continuous. In various embodiments, a cluster need not have a particular shape, and in various embodiments, a cluster may be required to have or not have a particular shape (e.g., curved, square or elongated). Such embodiments and variations thereof are contemplated to be within the scope of the present disclosure.

As mentioned above, the embodiments described above can be implemented separately, or two or more of the embodiments can be implemented in combination. Additionally, the examples may also be applied to implementations where each pixel is associated with a vector of image segmentation scores which refers to multiple categories. As mentioned in the example above, the multiple categories may be cat, dog, and sky, and each pixel has a vector of three scores that correspond to the three categories. In the case of each pixel having a vector of scores, the transformations described above may be performed for one category at a time, such that the transformations operate on a "layer" of scores of the same category.

Accordingly, described above are embodiments of transforming the image segmentation scores for pixels of an image to provide one or more image classification scores for the image. The embodiments described above can be implemented by a computing system, such as the computing system of FIG. 7, which will be described later herein. The embodiments described in connection with FIG. 4 are exemplary, and variations are contemplated to be within the scope of the present disclosure.

FIG. 5 shows another embodiment of block 220 (FIG. 2) for classifying an entire image based on the image segmentation scores for the pixels of the image. As mentioned above, each image segmentation score can indicate a probability that its corresponding pixel(s) are pixels of interest. At block 522, the operation involves accessing image segmentation scores for pixels of an image. At block 524, the operation involves determining a shape of pixels indicated to be pixels of interest based on the image segmentation scores, and/or determining a distribution of pixels indicated to be the pixels of interest based on the image segmentation scores. In the example of FIG. 3, the image segmentation scores 320 have sufficiently high probabilities to indicate that their corresponding pixels are pixels of interest. The shape of the corresponding pixels may be a rectangular shape, and the distribution of the corresponding pixels is highly clustered with very low location variation. In various embodiments, the shape of the pixels of interest may have other shapes (e.g., curved) and the distribution of the pixels of interest may have other distributions (e.g., scattered). In various embodiments, the shape of the pixels of interest and/or the distribution of the pixels of interest may be quantified. For example, the shape may be quantified based on the number of vertices and number of edges, among other things. In various embodiments, the shape may be determined by generating a mask based on the pixels of interest and determining if the shape of the mask corresponds with the shapes of objects of interest. As another example, the distribution may be quantified based on a spatial average and a spatial standard deviation, among other things. Other quantities related to shape and/or distribution are contemplated to be within the scope of the present disclosure. In various embodiments, the shape of the corresponding pixels and/or the distribution of the corresponding pixels may not be quantified. Rather, the shape and the distribution may be identified by the coordinates of all of the pixels of interest.

At block 526, the operation involves classifying the entire image based on the determined shape of the corresponding pixels and/or the determined distribution of the corresponding pixels. In various embodiments, the operation of block 526 can perform the classification by inputting the coordinates of the pixels of interest into a machine learning system which has been trained based on coordinates of pixels of interest. In various embodiments, the operation of block 526 can perform the classification by inputting the quantities representing the shape or distribution of the pixels of interest into a machine learning system which has been trained based on such quantities. Persons skilled in the art would understand how to implement and train such machine learning systems. In various embodiments, the operation of block 526 may be performed based on non-machine learning heuristics. For example, the heuristics may specify that the quantities representing the shape or distribution of the pixels of interest must fall within predetermined ranges, and operation of block 526 may classify the entire image based on such heuristics. Other types of heuristics are contemplated to be within the scope of the present disclosure.

The operation of block 526 can classify the image as an image which contains a particular element or characteristic, as an image which contains a particular anatomical feature, or as an image which contains a particular indicator of a disease, pathology, or condition, among other things, or as an image which does not contain any element or characteristic of interest, or as an image which does not contain any anatomical feature of interest, or as an image which does not contain any indicators of interest, among other possibilities. All such possibilities are contemplated to be within the scope of the present disclosure.

The operation of FIG. 5 is an example of the operation of block 220 of FIG. 2. The operations of FIG. 5 may be implemented on a computing system, such as the computing system of FIG. 7, which will be described in more detail below. Other operations for classifying an entire image based on the image segmentation scores for the pixels of the image are contemplated to be within the scope of the present disclosure.

Accordingly, described above are systems and methods for classifying an image based on image segmentation scores for the image. The disclosed systems and methods for classifying an image based on image segmentation scores for the image may be especially advantageous when the object of interest in an image occupies less than about 25%-30% of the image pixels. In various embodiments, the disclosed systems and methods may be particularly suitable when the object of interest in an image occupies less than about 10%-15% of the image pixels. However, the disclosed systems and methods can also operate effectively when the object of interest in an image occupies between 30%-50% of the image pixels. Additionally, the disclosed systems and methods may be advantageous when the color attributes of the object of interest may not differ significantly from the color attributes of the pixels surrounding the object of interest.

In accordance with aspects of the present disclosure, the following describes an exemplary operation for selecting images for a capsule endoscopy study based on image segmentations scores. As mentioned above, a capsule endoscopy device captures images as it travels naturally through the GIT. Images and additional data (e.g., metadata) may be transmitted to a wearable device that is worn by the patient. The procedure data (e.g., the captured images or a portion of them and additional metadata) may be stored on the storage device of the wearable device. The procedure data is downloaded to a computing device, which has an engine software stored thereon. Typically, the number of images transferred to be processed is on the order of tens of thousands and about 90,000 images on average. The received procedure data is then processed by the engine to a compiled study (or "study"). Reviewing thousands of images is a tedious task and may cause the reader to miss important information. Nevertheless, it is crucial that all images of medical importance will be included in the study. Accordingly, the processing and selection of CE images to be included in a CE study is very challenging and must be highly accurate, providing high sensitivity and specificity, while generating a study including as few images as possible.

Figure 6:
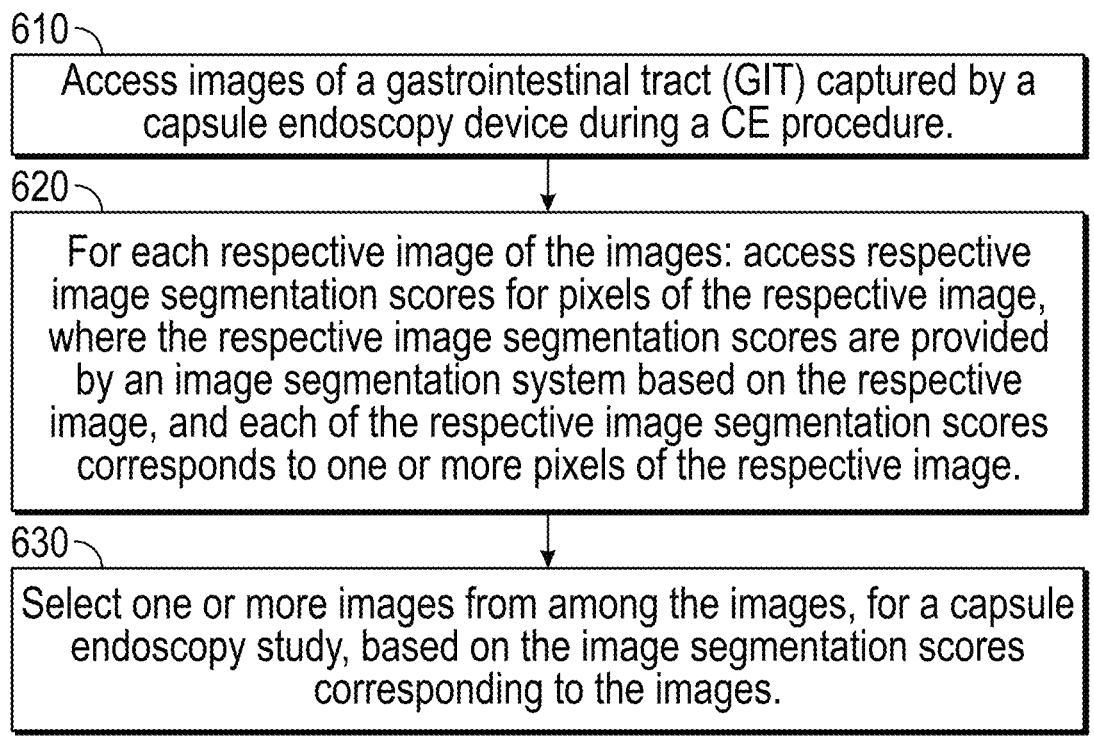
FIG. 6 is a flow diagram of an exemplary operation for selecting images for a capsule endoscopy study based on image segmentation scores, in accordance with aspects of the present disclosure.

FIG. 6 shows a flow diagram of an exemplary operation for selecting images for a compiled study based on image segmentation scores. At block 610, the operation involves accessing images of a gastrointestinal tract (GIT) captured by a capsule endoscopy device during a CE procedure. The accessed images may be images of the procedure data which are downloaded from the storage device of the wearable device to the computing device, or which are wirelessly uploaded from the storage device of the wearable device to a remote computer, such as a cloud platform. At block 620, the operation involves, for each respective image of the images, accessing respective image segmentation scores for pixels of the respective image. The respective image segmentation scores can be provided by an image segmentation system based on the respective image, where each of the respective image segmentation scores corresponds to one or more pixels of the respective image. At block 630, the operation involves selecting one or more images from among the images, for a capsule endoscopy study, based on the image segmentation scores corresponding to the images. In various embodiments, the operation of block 630 may select the one or more images by classifying the images based on the operations of FIG. 2, 4, or 5, and selecting images which have a particular classification or have particular classifications. For example, using the operation of FIG. 4, the operation of block 630 can transform the image segmentation scores for pixels of an image to provide one or more image classification scores for the image, and classify the entire image based on the image segmentation scores for the pixels of the image. Then, the operation can select images which have a particular classification or have particular classifications. In various embodiments, the operation of block 630 may operate to select one or more images from among the images, for a capsule endoscopy study, based on both classification scores derived from image segmentation score and based on other information derived from the image segmentation scores. For example, image classification scores can be derived based on the operations of FIG. 4, and other information, such as shape and distribution information described in connection with FIG. 5, can also be determined. Both the image classification scores and the additional information based on image segmentation scores can be used in the operation of block 630 to select images for a capsule endoscopy study. For example, shape information may be used to identify a pathology across multiple images, and tracking technology can be used to track such a pathology across multiple images. Aspects of image tracking are described in U.S. Provisional Application No. 63/018,870, filed May 1, 2020, which is hereby incorporated by reference herein in its entirety.

The operation of FIG. 6 is exemplary, and variations are contemplated to be within the scope of the present disclosure. For example, rather than capsule endoscopy images, other imaging technologies and other types of images may be used in the operation of FIG. 6. Accordingly, the operation of FIG. 6 can be applied to medical images or non-medical images and may be applied to a medical field or to any non-medical field. The operations of FIG. 6 can be implemented on a computing system, such as the computing system of FIG. 7, which is described below.

According to some aspects, each pixel may be associated with to a vector of image segmentation scores which refers to multiple categories. Such a vector of segmentation scores may be generated by using a single multi-category segmentation system or by using multiple segmentation systems, each determining one or more segmentation scores for one or more categories per pixel. As an example, the multiple categories may be different GI pathologies such as an ulcer and a polyp, and each pixel may be assigned with a vector of two scores that correspond to the two categories: ulcer and polyp. Accordingly, a multi-dimensional map of segmentation scores may be generated per image, where each dimension refers to pixel segmentation scores for a specific category. Analysis may be then performed, considering the different scores for the different categories per pixel and with respect to the entire image to obtain further information. Such analysis may be also based on classification scores or classifications assigned to the image for each one or more categories according to the disclosed systems and methods. In case multiple segmentation systems are used (e.g., by using multiple deep-learning segmentation networks or models), a normalization may be performed to enable comparison between image segmentation scores generated by the different networks.

Referring to FIG. 6, such a map of scores may be used for the task of CE image selection. With respect to block 630, the operation can select images which have image segmentation scores indicating presence of multiple categories, for example. In various embodiments, the multiple categories can correspond to multiple pathologies (e.g., each in a separate location in the image), and images which contain multiple pathologies may have a greater chance to be selected for the study.

In various embodiments, and as another example for a use of such a multi-category map of segmentation scores, an image may be suspected to include two categories, typically similar (e.g., similar GIT pathologies) at substantially the same image location. Analysis may be then performed to determine which is the most probable category (e.g., to determine the type of pathology suspected to be included in the image). In various embodiments, an image may be suspected to include two categories (e.g., GIT pathologies) at substantially the same image location, indicating a mutual event, such as an ulcerated polyp. An ulcerated polyp, for example, is a polyp of a higher degree of severity and thus such an identification may provide clinically important information. In various embodiments, identifying two types of categories in the same image, i.e., located adjacently, may be of interest. For example, in CE images, identifying a bleeding and a source of bleeding (e.g., an ulcer) in the same image may provide clinically important information. Using the multi-category map of segmentation scores and optionally in addition to classifying the image according to the different categories according to the disclosed systems and methods, may facilitate such identifications and provide important information.

Figure 7:
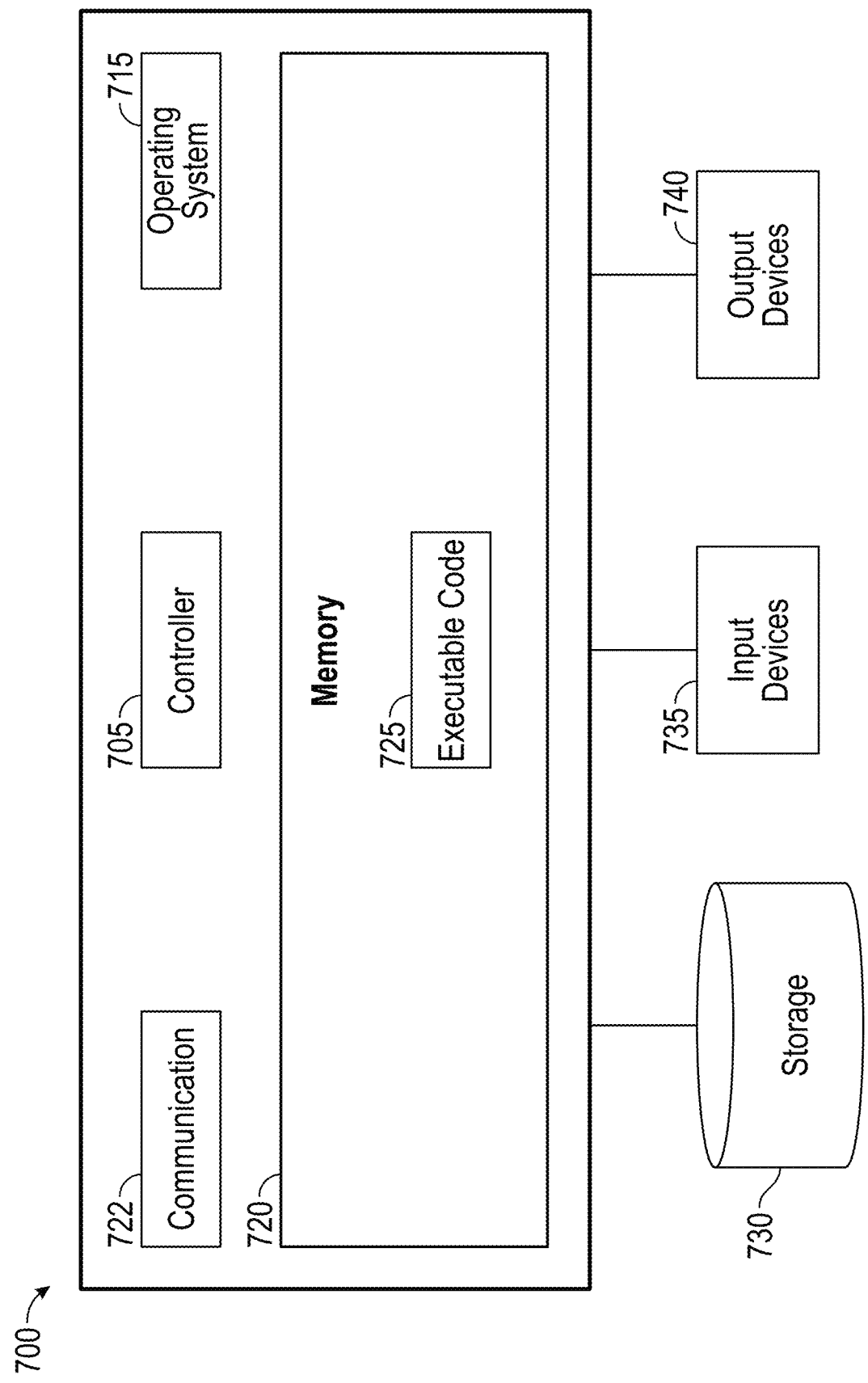
FIG. 7 is a block diagram of exemplary components of a computing system for implementing the disclosed operations, in accordance with aspects of the present disclosure.

FIG. 7 shows a block diagram of an exemplary computing system 700 that may implement the operations of the present disclosure. The computing system 700 may be a standalone computing system, a distributed computing system, or a cloud computing system, or some combination thereof. Exemplary system architectures which may include illustrated computing system 700 are described in International Publication No. WO2020/236683, which is hereby incorporated by reference herein in its entirety.

The illustrated computing system 700 includes a processor or controller 705, which may be or include, for example, one or more central processing unit processor(s) (CPU), one or more Graphics Processing Unit(s) (GPU or GPGPU), a chip or any suitable computing or computational device. The computing system 700 also includes an operating system 715, a memory 720, a communication component 722, a storage 730, input devices 735, output devices 740. The communication component 722 of the computing system 300 may allow communications with remote or external devices, e.g., via the Internet or another network, via radio, or via a suitable network protocol such as File Transfer Protocol (FTP), etc.

The operating system 715 may be or may include any code segment designed and/or configured to perform tasks involving coordination, scheduling, arbitration, supervising, controlling, and/or managing operations of the computing system 700, such as scheduling execution of programs. The memory 720 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. The memory 720 may be or may include a plurality of possibly different memory units and may store, for example, instructions to carry out an operation (e.g., FIG. 2, 4, 5, or 6), and/or data such as images, image segmentation scores, and/or image classification scores.

Executable code 725 may be any executable code, e.g., an application, a program, a process, task, or script. Executable code 725 may be executed by controller 705, possibly under the control of operating system 715. For example, execution of executable code 725 may cause the classification or selection of medical images as described herein. In some systems, more than one computing system 700 may be used for the operations described herein. One or more processor(s) 705 may be configured to carry out operations of the present disclosure by, for example, executing software or code.

Storage 730 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image segmentation scores, and/or image classification scores, among other things, may be stored in storage 730 and may be loaded from storage 730 into memory 720 where it may be processed by controller 705. In some embodiments, some of the components shown in FIG. 7 may be omitted.

Input devices 735 may include, for example, a mouse, a keyboard, a touch screen or pad, or any suitable input device. It will be recognized that any suitable number of input devices may be operatively coupled to computing system 700. Output devices 740 may include one or more monitors, screens, displays, speakers and/or any other suitable output devices. It will be recognized that any suitable number of output devices may be operatively coupled to computing system 700 as shown by block 740. Any applicable input/output (I/O) devices may be operatively coupled to computing system 700, such as a wired or wireless network interface card (NIC), a modem, printer or facsimile machine, a universal serial bus (USB) device or external hard drive.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, Python, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other metalanguages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A classification system for classifying images, comprising:
    one or more processors; and
    at least one memory storing machine executable instructions which, when executed by the one or more processors, cause the classification system to:
        input an image captured by a capsule endoscopy device during a CE procedure to a deep learning neural network to generate image segmentation scores for pixels of the image, each of the image segmentation scores corresponding to at least one pixel of the pixels of the image, and classify the entire image based on the image segmentation scores for the pixels of the image, wherein each of the image segmentation scores indicates a probability of the corresponding at least one pixel being a pixel of interest or not being a pixel of interest.

2. The classification system of claim 1, wherein the instructions, when executed by the one or more processors, further cause the classification system to transform the image segmentation scores for the pixels of the image to provide at least one image classification score,
wherein classifying the entire image comprises classifying the image based on at least the at least one image classification score.

3. The classification system of claim 2, wherein in transforming the image segmentation scores, the instructions, when executed by the one or more processors, cause the classification system to perform at least one of: an inference of a machine learning system or a non-machine learning transformation operation.

4. The classification system of claim 3, wherein the non-machine learning transformation operation comprises determining a maximum score among the image segmentation scores for the pixels of the image,
wherein classifying the entire image comprises classifying the entire image based on the maximum score.

5. The classification system of claim 3, wherein the non-machine learning transformation operation comprises determining at least one of:
an average score of a predetermined number of highest image segmentation scores among the image segmentation scores for the pixels of the image, or
a count of the image segmentation scores for the pixels of the image having a value above a threshold,
wherein classifying the entire image comprises classifying the entire image based on at least one of: the average score or the count.

6. The classification system of claim 3, wherein the non-machine learning transformation operation comprises:
identifying a cluster of pixels of the image corresponding to a cluster of highest image segmentation scores among the image segmentation scores for the pixels of the image; and
determining an average score of the cluster of highest image segmentation scores,
wherein classifying the entire image comprises classifying the entire image based on the average score of the cluster.

7. The classification system of claim 1, wherein the image segmentation scores for the pixels of the image comprise scores indicating whether a pixel is a background pixel or a pixel of interest,
wherein the instructions, when executed by the one or more processors, cause the classification system to further perform at least one of:
determining a shape of pixels indicated to be pixels of interest based on the image segmentation scores, or
determining a distribution of pixels indicated to be the pixels of interest based on the image segmentation scores,
wherein classifying the entire image comprises classifying the entire image based on at least one of: the determined shape or the determined distribution.

8. The classification system of claim 1, wherein each score of the image segmentation scores corresponds to one pixel of the pixels of the image.

9. A classification method for classifying images, comprising:
inputting an image captured by a capsule endoscopy device during a CE procedure to a deep learning neural network to generate image segmentation scores for pixels of the image, each of the image segmentation scores corresponding to at least one pixel of the pixels of the image, and
classifying the entire image based on the image segmentation scores for the pixels of the image, wherein each of the image segmentation scores indicates a probability of the corresponding at least one pixel being a pixel of interest or not being a pixel of interest.

10. The classification method of claim 9, further comprising transforming the image segmentation scores for the pixels of the image to provide at least one image classification score,
wherein classifying the entire image comprises classifying the entire image based on at least the at least one image classification score.

11. The classification method of claim 10, wherein transforming the image segmentation scores comprises performing at least one of: an inference of a machine learning classifier or a non-machine learning transformation operation.

12. The classification method of claim 11, wherein the non-machine learning transformation operation comprises determining a maximum score among the image segmentation scores for the pixels of the image,
wherein classifying the entire image comprises classifying the entire image based on the maximum score.

13. The classification method of claim 11, wherein the non-machine learning transformation operation comprises determining at least one of:
an average score of a predetermined number of highest image segmentation scores among the image segmentation scores for the pixels of the image, or
a count of the image segmentation scores for the pixels of the image having a value above a threshold,
wherein classifying the entire image comprises classifying the entire image based on at least one of: the average score or the count.

14. The classification method of claim 11, wherein the non-machine learning transformation operation comprises:
identifying a cluster of pixels of the image corresponding to a cluster of highest image segmentation scores among the image segmentation scores for the pixels of the image; and
determining an average score of the cluster of highest image segmentation scores,
wherein classifying the entire image comprises classifying the entire image based on the average score of the cluster.

15. The classification method of claim 9, wherein the image segmentation scores for the pixels of the image comprise scores indicating whether a pixel is a background pixel or a pixel of interest,
the classification method further comprising performing at least one of:
determining a shape of pixels indicated to be pixels of interest based on the image segmentation scores, or
determining a distribution of pixels indicated to be pixels of interest based on the image segmentation scores,
wherein classifying the entire image comprises classifying the entire image based on at least one of: the determined shape or the determined distribution.

16. The classification method of claim 9, wherein each score of the image segmentation scores corresponds to one pixel of the pixels of the image.

17. An image selection system for selecting images of a gastrointestinal tract, comprising:
- one or more processors; and
- at least one memory storing machine executable instructions which, when executed by the one or more processors, cause the image selection system to:
  - access a plurality of images of a gastrointestinal tract (GIT) captured by a capsule endoscopy device during a CE procedure;
  - for each respective image of the plurality of images: input the respective image to a deep learning neural network to generate respective image segmentation scores for pixels of the respective image, each of the respective image segmentation scores corresponding to at least one pixel of the pixels of the respective image, wherein each of the image segmentation scores indicates a probability of the corresponding at least one pixel being a pixel of interest or not being a pixel of interest; and
  - select at least one image from among the plurality of images for a capsule endoscopy study based on the image segmentation scores corresponding to the plurality of images.

18. The image selection system of claim 17, wherein the instructions, when executed by the one or more processors, further cause the image selection system to:
- for each image of the plurality of images: compute at least one respective image classification score for the respective image based at least on the respective image segmentation scores for the pixels of the respective image,
- wherein selecting at least one image from among the plurality of images based on the respective image segmentation scores includes selecting at least one image from among the plurality of images for the capsule endoscopy report based on at least the image classification scores computed from the image segmentation scores corresponding to the plurality of images.

* * * * *